United States Patent
Miyake et al.

(10) Patent No.: US 8,192,354 B2
(45) Date of Patent: Jun. 5, 2012

(54) ENDOSCOPE INSERTED-SHAPE DETECTING APPARATUS

(75) Inventors: Kensuke Miyake, Hachioji (JP); Yoshitaka Miyoshi, Hachioji (JP); Chieko Aizawa, Hachioji (JP); Fumiyuki Onoda, Tama (JP); Minoru Sato, Hino (JP); Hiroshi Niwa, Koganei (JP); Tomohiko Oda, Kawagoe (JP)

(73) Assignee: Olympus Corporation, Tokyo (JP)

( * ) Notice: Subject to any disclaimer, the term of this patent is extended or adjusted under 35 U.S.C. 154(b) by 1407 days.

(21) Appl. No.: 11/807,496

(22) Filed: May 29, 2007

(65) Prior Publication Data
US 2007/0232854 A1 Oct. 4, 2007

Related U.S. Application Data

(63) Continuation of application No. PCT/JP2005/021988, filed on Nov. 30, 2005.

(30) Foreign Application Priority Data

Dec. 1, 2004 (JP) ................................ 2004-348945

(51) Int. Cl.
*A61B 1/00* (2006.01)
*A61B 1/04* (2006.01)
(52) U.S. Cl. ........................................ 600/117; 600/145
(58) Field of Classification Search .................. 600/102, 600/117, 145, 146
See application file for complete search history.

(56) References Cited

U.S. PATENT DOCUMENTS

| 5,253,647 | A | | 10/1993 | Takahashi et al. |
| 5,681,260 | A | * | 10/1997 | Ueda et al. ..................... 600/114 |
| 5,729,129 | A | | 3/1998 | Acker |
| 5,997,473 | A | * | 12/1999 | Taniguchi et al. ............. 600/117 |
| 6,059,718 | A | * | 5/2000 | Taniguchi et al. ............. 600/117 |
| 6,511,417 | B1 | | 1/2003 | Taniguchi et al. |
| 6,745,065 | B2 | * | 6/2004 | Niwa et al. ..................... 600/424 |
| 6,773,393 | B1 | | 8/2004 | Taniguchi et al. |
| 6,773,394 | B2 | | 8/2004 | Taniguchi et al. |
| 7,706,859 | B2 | * | 4/2010 | Aizawa et al. ................. 600/424 |
| 2003/0055317 | A1 | | 3/2003 | Taniguchi et al. |
| 2004/0204645 | A1 | * | 10/2004 | Saadat et al. .................. 600/424 |

FOREIGN PATENT DOCUMENTS

| JP | 11-325810 | 11/1999 |
| JP | 2000-081304 | 3/2000 |
| JP | 2002-131009 | 5/2002 |

* cited by examiner

*Primary Examiner* — Philip R Smith
(74) *Attorney, Agent, or Firm* — Scully, Scott, Murphy & Presser, P.C.

(57) ABSTRACT

An endoscope inserted-shape detecting apparatus 8 includes a sense coil unit 23 in which multiple sense coil groups of sense coil groups 23A to 23I for detecting magnetic fields generated by multiple source coils 21 in an inserted-shape detecting probe 6 are placed as a part of the endoscope inserted-shape detecting apparatus 8, a signal detecting section 33, a source coil position analyzing section 35 and a signal control section 37 that selects a magnetic-field detecting element to be used for detection of a magnetic field signal based on the magnetic field generated by each of the source coils 21 from the sense coil groups 23A to 23I in a control section based on positional information signals outputted from the source coil position analyzing section 35.

18 Claims, 9 Drawing Sheets

ENDOSCOPE INSERTED-SHAPE DETECTING APPARATUS

CROSS REFERENCE TO RELATED APPLICATION

This application is a continuation application of PCT/JP2005/021988 filed on Nov. 30, 2005 and claims benefit of Japanese Application No. 2004-348945 filed in Japan on Dec. 1, 2004, the entire contents of which are incorporated herein by this reference.

BACKGROUND OF THE INVENTION

1. Field of the Invention

The present invention relates to an endoscope inserted-shape detecting apparatus and, in particular to an endoscope inserted-shape detecting apparatus that can detect the shape of an insertion section of an endoscope inserted to a subject.

2. Description of the Related Art

Conventionally, an endoscope has been widely used in medical fields, industrial fields and so on. In a medical field, an endoscope is used for performing various treatments on a predetermined part or a predetermined tissue of a body cavity of a living body, which is an affected part. In particular, in order to insert an endoscope from the anus side of a living body to perform various processing on a lower digestive tract and to insert the insertion section into a curving body cavity smoothly, an endoscope inserted-shape detecting apparatus that can detect the position of the insertion section within the body cavity, a curving state and so on is used also with an endoscope.

An endoscope inserted-shape detecting apparatus as described above has been proposed in Japanese Unexamined Patent Application Publication No. 2000-081304, for example. An endoscope inserted-shape detecting apparatus disclosed in Japanese Unexamined Patent Application Publication No. 2000-081304 has a configuration and operation for displaying the inserted shape of an insertion section of an endoscope on a monitor by detecting a magnetic field generated from a source coil deployed in a probe within an insertion section of an electronic endoscope as signals by a detecting block through a sense coil and then performing signal processing on the signals by a host processor.

SUMMARY OF THE INVENTION

An endoscope inserted-shape detecting apparatus according to one aspect of the present invention includes a magnetic-field detecting section having multiple magnetic-field detecting elements at predetermined positions for detecting the magnetic-fields generated by multiple magnetic-field generating elements placed in an insertion section of an endoscope, a signal detecting section outputting the magnetic fields detected by the magnetic-field detecting elements as magnetic field signals, a magnetic-field generated position estimating section estimating the position of the magnetic-field generating element based on the magnetic field signals, and a control section selecting the magnetic-field detecting element to be used for the detection of magnetic field signals based on the estimation result by the magnetic-field generated position estimating section.

DETAILED DESCRIPTION OF THE PREFERRED EMBODIMENT(S)

With reference to drawings, examples of the present invention will be described below.

First Embodiment

Figure 1:
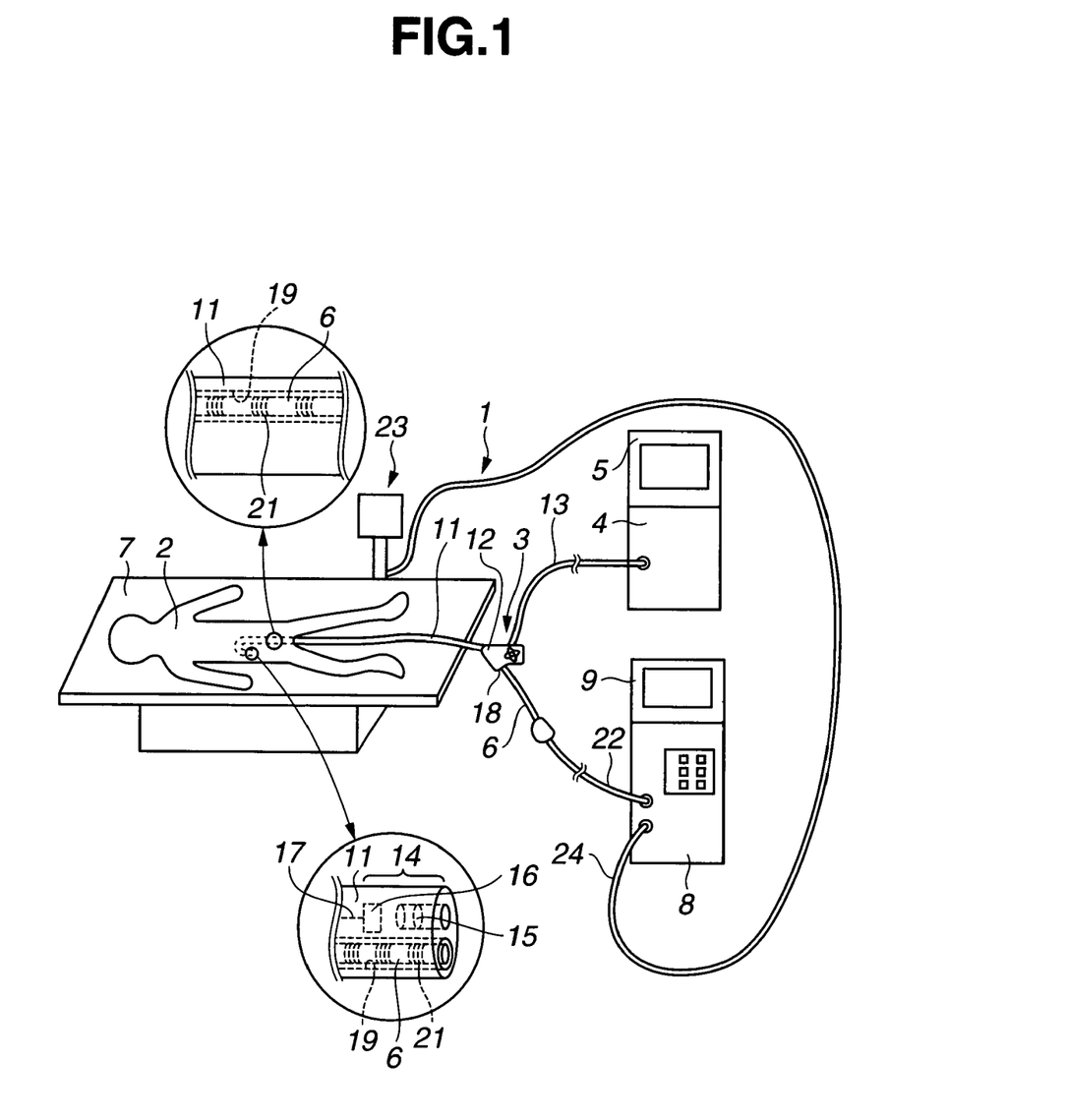
FIG. 1 is a diagram showing an entire configuration of an endoscopic system according to a first embodiment of the present invention.
Figure 2:
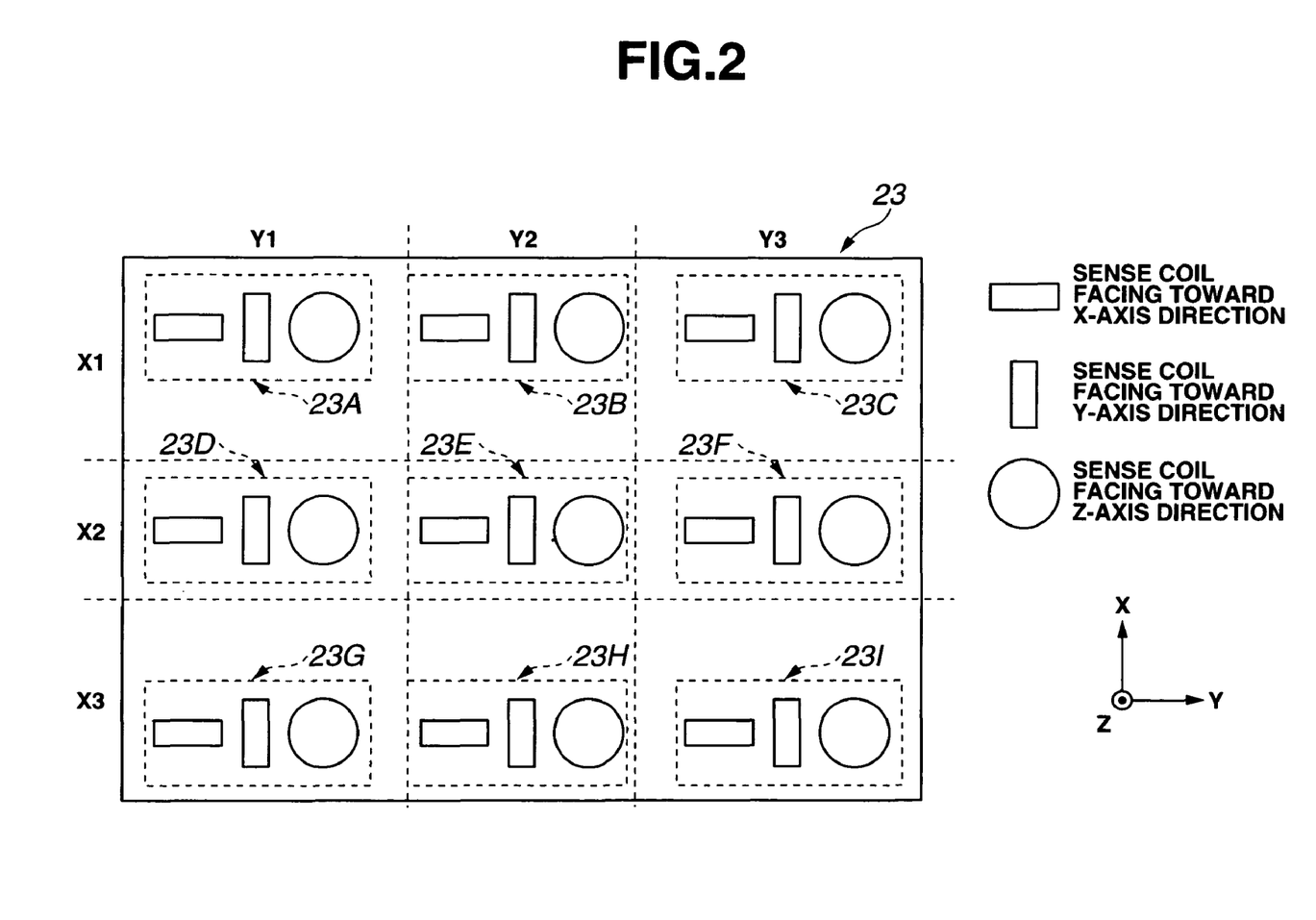
FIG. 2 is a diagram showing a configuration of a sense coil unit according to the first embodiment.
Figure 3:
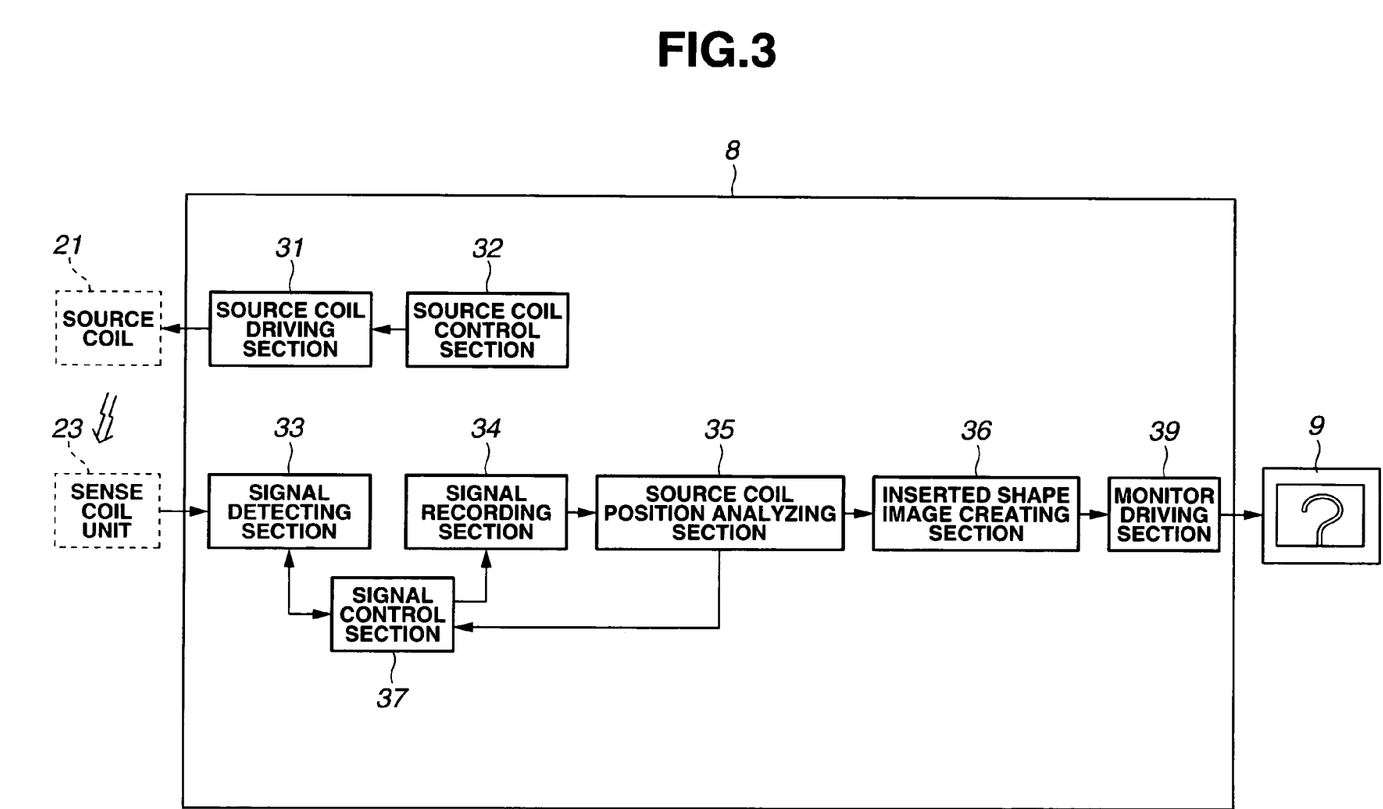
FIG. 3 is a block diagram showing an internal configuration of the endoscope inserted-shape detecting apparatus according to the first embodiment.
Figure 4:
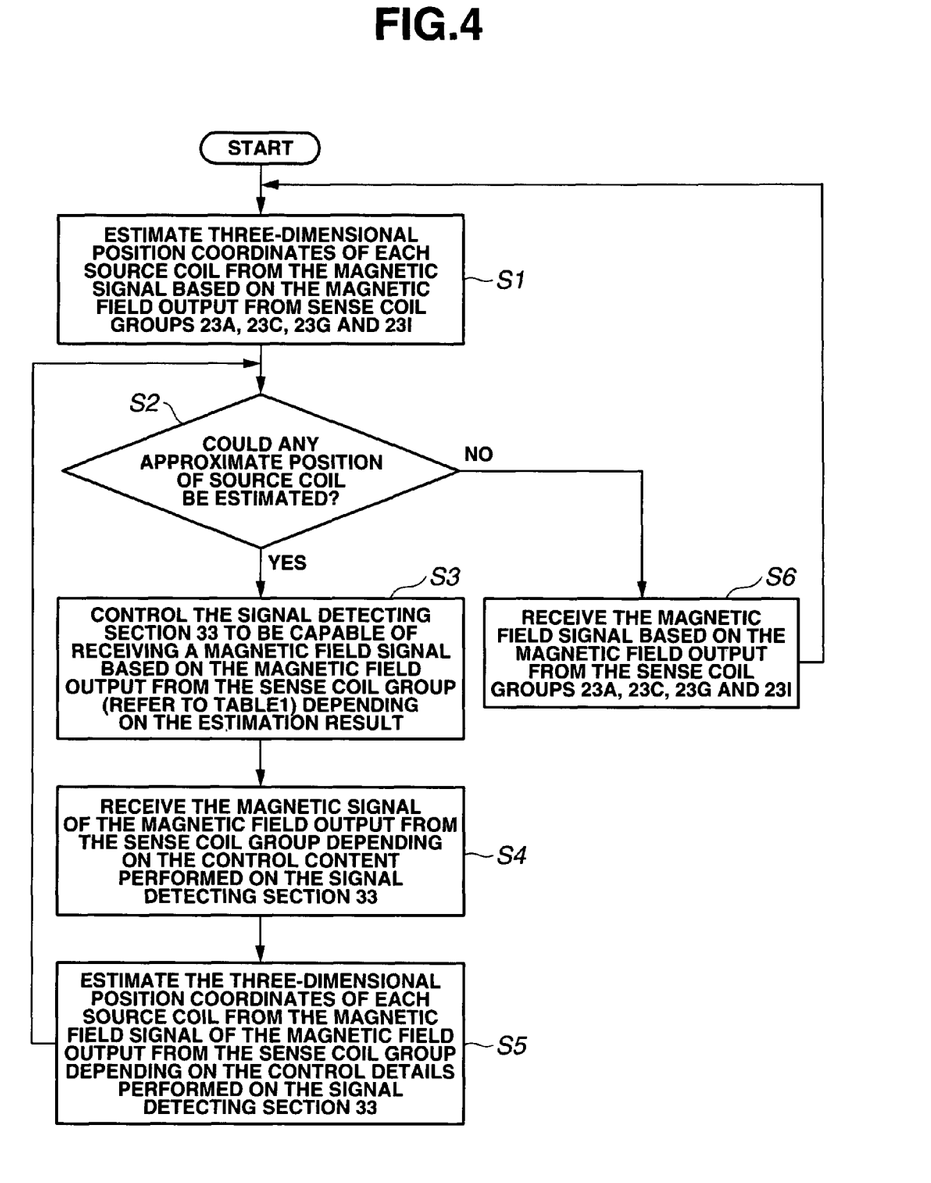
FIG. 4 is a flowchart showing content of the control to be performed by the endoscope inserted-shape detecting apparatus according to the first embodiment.

FIGS. 1 to 4 relate to a first embodiment of the present invention. FIG. 1 is a diagram showing an entire configuration of an endoscopic system according to a first embodiment of the present invention. FIG. 2 is a diagram showing a configuration of a sense coil unit according to the first embodiment. FIG. 3 is a block diagram showing an internal configuration of the endoscope inserted-shape detecting apparatus according to the first embodiment. FIG. 4 is a flowchart showing content of the control to be performed by the endoscope inserted-shape detecting apparatus according to the first embodiment.

An endoscopic system 1 mainly includes, as shown in FIG. 1, an endoscope 3, a video processor 4, a monitor 5, an inserted-shape detecting probe 6, a bed 7, an endoscope inserted-shape detecting apparatus 8, a monitor 9, and a sense coil unit 23. The endoscope 3 picks up an image of the inside of a body cavity of a patient 2, which is a subject, within the body cavity and outputs the picked-up image of the inside of the body cavity as image pickup signals. The video processor 4 performs image processing on image pickup signals outputted from the endoscope 3 to output. The monitor 5 displays an image of a desired part picked up by the endoscope 3 based on image pickup signals outputted from the video processor 4. The patient 2 is laid down on the bed 7.

The endoscope 3 includes an insertion section 11, an operation section 12 and a universal cord 13. The insertion section 11 is to be inserted into a body cavity, for example. The operation section 12 is provided on the proximal end side of the insertion section 11 for operating by grasping the endoscope 3. The universal cord 13 extends from a side of the operation section 12 and is connectable to an external apparatus such as the video processor 4.

The distal end portion 14, which is the distal end of the insertion section 11, internally includes an objective optical system 15 and a CCD (solid image pickup device) 16. The objective optical system 15 is used for forming an image of a subject. The CCD 16 picks up an image of the subject, which is formed by the objective optical system 15, and outputs the picked-up image of the subject as image pickup signals. The image pickup signals outputted from the CCD 16 are outputted to a signal line 17 having one end connected to the back of the CCD 16. The signal line 17 is internally contained through the insertion section 11, operation section 12 and universal cord 13 and has the other end electrically connected to the video processor 4. Therefore, the image pickup signals outputted from the CCD 16 are outputted to the video processor 4 through the signal line 17.

One side of the operation section 12 has a probe insertion opening 18 for inserting the inserted-shape detecting probe 6. The probe insertion opening 18 connects to a probe channel 19 provided internally through the insertion section 11 so that the inserted-shape detecting probe 6 can be internally contained through the probe channel 19.

The inserted-shape detecting probe 6 has a dimension and a shape, for example, which can be inserted to the probe insertion opening 18 and probe channel 19 of the endoscope 3, and multiple source coils 21 are spaced apart at predetermined intervals.

The source coils 21 are a part of the endoscope inserted-shape detecting apparatus 8 and are configured as magnetic-field generating elements functioning as a magnetic-field generating section, and the inserted-shape detecting probe 6 inserted in the endoscope 3 generates a magnetic field depending on the inserted shape of the insertion section 11.

A cable 22 for connecting to the endoscope inserted-shape detecting apparatus 8 extends from the proximal end side of the inserted-shape detecting probe 6. The endoscope inserted-shape detecting apparatus 8 generates a magnetic field by driving the source coils 21 through the cable 22.

The sense coil unit 23, which is a magnetic-field detecting section, provided outside of the endoscope inserted-shape detecting apparatus 8 as a part of the endoscope inserted-shape detecting apparatus 8 is placed at a position as shown in FIG. 1 such that the magnetic field generated by each of the multiple source coils 21 provided in the inserted-shape detecting probe 6 to be inserted to the probe channel 19 of the insertion section 11 within a body cavity of the patient 2 laid on the bed 7 can be detected and is connected to the endoscope inserted-shape detecting apparatus 8 through a cable 24.

The sense coil unit 23 includes sense coil groups 23A, 23B, 23C, 23D, 23E, 23F, 23G, 23H and 23I as nine magnetic-field detecting elements. The sense coil groups 23A to 23I above are placed in a matrix form within the sense coil unit 23 as shown in FIG. 2.

The sense coil group 23A includes, as shown in FIG. 2, three sense coils of a sense coil facing toward the X-axis direction, a sense coil facing toward the Y-axis direction and a sense coil facing toward the Z-axis direction. Other sense coil groups other than the sense coil group 23A also has the same configuration as that of the sense coil group 23A.

Then, the magnetic fields detected by the sense coil groups 23A to 23I are outputted to the endoscope inserted-shape detecting apparatus 8. Notably, the sense coil unit 23 is not limitedly placed at the position described above but may be placed within the bed 7, for example. The number of the sense coil groups within the sense coil unit 23 is not limited to nine arranged in a matrix form as shown in FIG. 2 but may be any number other than nine, and the sense coil groups may not be placed in a matrix form. Furthermore, each of the sense coil groups within the sense coil unit 23 is not limited to the one having three sense coils as described above but may have one sense coil only, for example.

As shown in FIG. 3, the endoscope inserted-shape detecting apparatus 8 internally includes a source coil driving section 31, a source coil control section 32, a signal detecting section 33, a signal recording section 34, a source coil position analyzing section 35, an inserted-shape image creating section 36, a signal control section 37 and a monitor driving section 39. The source coil driving section 31 drives each of the source coils 21. The source coil control section 32 controls the source coils 21 through the source coil driving section 31 such that the source coils 21 can generate magnetic fields at predetermined times and predetermined different frequencies.

The signal detecting section 33 converts the magnetic fields to magnetic field signals based on the magnetic fields outputted from the sense coil unit 23 and then amplifies to a signal-processable level and outputs the magnetic field signal based on the magnetic field outputted from the magnetic-field detecting element in a predetermined positional relationship with the source coils 21 or a predetermined source coil 21 among the magnetic field signals. Notably, the control content of the signal control section 37 will be described later.

The signal control section 37, which is a control section, outputs the magnetic field signal outputted from the signal detecting section 33 to the signal recording section 34. The signal control section 37 has a threshold value based on the positions where the sense coil groups 23A to 23I are placed on each of the X-, Y- and Z-coordinates in the sense coil unit 23. The signal control section 37 controls the signal detecting section 33 based on the threshold values and positional information signals, which are signals including position information of the source coils 21 outputted from the source coil position analyzing section 35 to be capable of receiving the magnetic field signal based on the magnetic field outputted from the sense coil group in a predetermined positional relationship with each of the source coils 21 among the sense coil groups 23A to 23I. The signal control section 37 is not limited to a hardware configuration but may be configured as software that performs the above-described control content within the signal detecting section 33. The control to be performed by the signal control section 37 is not limited to the above-described content but may be performed only to receive a predetermined number of magnetic field signals having a predetermined signal level, which is required for estimating the position of each of the source coils 21 among the magnetic field signals outputted from the signal detecting section 33. More specifically, the control to be performed by the signal control section 37 may be performed to receive, from the signal detecting section 33, the magnetic field signal only based on the magnetic field outputted from four sense coil groups in order from the one having a lower signal level than that causing the magnetic saturation and having a higher signal level among the nine sense coil groups 23A to 23I.

The signal recording section 34 temporarily records the magnetic field signal outputted from the signal control section 37.

The source coil position analyzing section 35, which is a magnetic-field generated position estimating section, estimates the three-dimensional position coordinates of each of the source coils 21 based on the magnetic field signal recorded in the signal recording section 34 and outputs the result as a position information signal.

The inserted-shape image creating section 36 calculates the three-dimensional shape of the insertion section 11 based on the position information signal of each of the source coils 21 outputted from the source coil position analyzing section 35. The inserted-shape image creating section 36 creates an inserted-shape figure of the insertion section 11 from the calculated three-dimensional shape of the insertion section 11 and outputs the figure as an inserted-shape figure signal.

The monitor driving section 39 drives the monitor 9 based on the inserted-shape figure signal outputted from the inserted-shape image creating section 36 and renders the inserted-shape figure of the insertion section 11 on the monitor 9.

Next, with reference to FIGS. 1 to 4, an operation by using the endoscopic system 1 according to the present embodiment will be described.

First, a surgeon inserts the inserted-shape detecting probe 6 to the endoscope 3 from the probe insertion opening 18. After that, the surgeon connects the universal cord 13 of the endoscope 3 to the video processor 4 and connects the cable 22 of the inserted-shape detecting probe 6 and the cable 24 extending from the sense coil unit 23 to the endoscope inserted-shape detecting apparatus 8 and inserts the insertion section 11 of the endoscope 3 into a body cavity of the patient 2. Then, the CCD 16 picks up an image of the inside of the body cavity and outputs the picked up image of the inside of the body cavity as an image pickup signal. Then, the video processor 4 may perform image processing, for example, based on the image pickup signal outputted from the CCD 16 and output the image pickup signal having undergone the image processing, for example, to the monitor 5. The monitor 5 displays the image of the inside of the body cavity, which is picked up by the endoscope 3, based on the image pickup signal outputted from the video processor 4.

The source coil control section 32 of the endoscope inserted-shape detecting apparatus 8 controls the source coils 21 through the source coil driving section 31 such that the source coils 21 can generate magnetic fields at different times. The source coils 21 generate magnetic fields depending on the inserted shape of the insertion section 11 within the body cavity based on the control content of the source coil control section 32.

After each of the source coils 21 starts generating a magnetic field, the sense coil unit 23 first detects the magnetic field generated from each of the source coils 21 through the sense coil groups 23A to 23I placed in a matrix form as shown in FIG. 2. The magnetic fields detected by the sense coil groups 23A to 23I are outputted to the endoscope inserted-shape detecting apparatus 8 through the cable 24.

The signal detecting section 33 converts the magnetic fields to magnetic field signals based on the magnetic fields outputted from the sense coil unit 23 and then amplifies to a signal-processable level and outputs the magnetic field signals based on the magnetic fields outputted from the sense coil groups 23A, 23C, 23G and 23I, that is, magnetic field signals from twelve sense coils of the four sense coil groups among the magnetic field signals. The signal control section 37 outputs magnetic field signals of the twelve sense coils of the four groups, which are outputted from the signal detecting section 33, to the signal recording section 34. The signal recording section 34 temporarily records a magnetic signal outputted from the signal control section 37. The source coil position analyzing section 35 estimates the three-dimensional position coordinates of each of the multiple source coils 21 based on the magnetic field signals of the twelve sense coils of the four groups recorded in the signal recording section 34 (in step S1 in FIG. 4) and outputs the result of the estimation to the signal control section 37 as positional information signals.

If there is a source coil of the multiple source coils 21 even the approximate position of which cannot be estimated by the source coil position analyzing section 35 (in step S2 in FIG. 4) since the entire body of the inserted-shape detecting probe 6 is not inserted into a body cavity of the patient 2, for example, the signal control section 37 based on the positional information signals outputted from the source coil position analyzing section 35 receives the magnetic field signals of the twelve sense coils of the four groups 23A, 23C, 23G and 23I based on the magnetic fields outputted from the sense coil groups through the signal detecting section 33 again (in step S6 in FIG. 4) and outputs the magnetic signals to the signal recording section 34 in order to estimate the position of the source coil again. Then, the source coil position analyzing section 35 estimates the three-dimensional position coordinates of the source coil again based on the magnetic field signals of the twelve sense coils of the four groups, which are recorded in the signal recording section 34 (in step S1 in FIG. 4) and outputs the result of the estimation to the signal control section 37 as the positional information signal.

The signal control section 37 further controls the signal detecting section 33 based on the positional information signals outputted from the source coil position analyzing section 35 to be capable of receiving the magnetic field signals based on the magnetic fields from the sense coil groups in a predetermined positional relationship, that is, in a positional relationship, which allows the estimation of the positions of the source coils with high accuracy, with the source coils, the approximate positions of which can be estimated at least by the source coil position analyzing section 35 (in step S2 in FIG. 4) of the multiple source coils 21.

The following description assumes that the sense coil unit 23 is divided into virtual areas as shown in FIG. 2 in accordance with the layout of the sense coil groups 23A through 23I. It is further assumed that the signal control section 37 has a value for dividing the whole of the entire sense coil unit 23 into the virtual areas as the threshold values in the X- and Y-axes. The following description is on one example in which a predetermined source coil 21, which is a subject of the estimation, is estimated as being in an area where an area X1 and an area Y1 cross (which will be called area (X1,Y1) below) and where the position in the Z-axis direction is at a coordinate of Z1 based on the estimation by the source coil position analyzing section 35.

If the predetermined source coil 21 to be estimated is in an area (X1,Y1,Z1) where Z1<α (where α is a real number), that is, at a position extremely near the sense coil group 23A in the area (X1,Y1), the accuracy may be possibly reduced for estimating the position of the predetermined source coil 21 by the source coil position analyzing section 35 due to magnetic saturation, for example. In order to prevent the reduction of the accuracy for the position estimation due to magnetic saturation above, the signal control section 37 controls the signal detecting section 33 to be capable of receiving magnetic field signals of the twelve sense coils of the four sense coil groups 23C, 23F, 23H and 23I based on the magnetic fields outputted from the sense coil groups as shown on TABLE 1, which will be described later (in step S3 in FIG. 4).

If the predetermined source coil 21 to be estimated is in the area (X1,Y1,Z1) where $\alpha \leq Z1 \leq \beta$ (where β is a real number where $\alpha \leq \beta$), that is, at a position between the coordinates α and β on the Z-axis in the area (X1,Y1), the signal control section 37 controls the signal detecting section 33 to be capable of receiving magnetic field signals of the twelve sense coils of the four sense coil groups 23A, 23B, 23D and 23E based on the magnetic fields outputted from the sense coil groups as shown on TABLE 1, which will be described later (in step S3 in FIG. 4) in order to optimize the strength of the magnetic field to be detected.

If the predetermined source coil 21 to be estimated is in an area (X1,Y1,Z1) where Z1>$\beta$, that is, at a position far from the sense coil group 23A in the area (X1,Y1), the accuracy may be possibly reduced for estimating the position of the predetermined source coil 21 by the source coil position analyzing section 35 due to the fact that the magnetic field to be detected is extremely weak, for example. In order to prevent the reduction of the accuracy for the position estimation due to the fact that the magnetic field to be detected is extremely weak as described above, the signal control section 37 controls the signal detecting section 33 to be capable of receiving magnetic field signals of the twelve sense coils of the four sense coil groups 23A, 23C, 23G and 23I based on the magnetic fields outputted from the sense coil groups as shown on TABLE 1, which will be described later (in step S3 in FIG. 4).

The signal control section 37 defines the sense coil groups for receiving magnetic field signals from all of the multiple source coils 21 in the inserted-shape detecting probe 6 based on a template including threshold values of the X- and Y-co-ordinates, which are values dividing the entire sense coil unit 23 into the virtual areas and a threshold value of the Z-coordinate, which are coordinates $\alpha$ and $\beta$, as shown on TABLE 1 below.

TABLE 1

| Position In Z-Axis Direction | Position In X-Axis Direction | Position In Y-Axis Direction | Sense Coil Groups Used For Receiving Magnetic Field Outputted From Each Source Coil 21 |
|---|---|---|---|
| $Z < \alpha$ | X1 | Y1 | 23C, 23F, 23H and 23I |
|  | X1 | Y2 | 23B, 23C, 23F and 23I |
|  | X1 | Y3 | 23B, 23C, 23F and 23I |
|  | X2 | Y1 | 23D, 23G, 23H and 23I |
|  | X2 | Y2 | 23A, 23C, 23G and 23I |
|  | X2 | Y3 | 23A, 23B, 23C and 23D |
|  | X3 | Y1 | 23D, 23G, 23H and 23I |
|  | X3 | Y2 | 23A, 23B, 23D and 23G |
|  | X3 | Y3 | 23A, 23B, 23D and 23G |
| $\alpha \leq z \leq \beta$ | X1 | Y1 | 23A, 23B, 23D and 23E |
|  | X1 | Y2 | 23A, 23B, 23G and 23H |
|  | X1 | Y3 | 23D, 23E, 23G and 23H |
|  | X2 | Y1 | 23A, 23C, 23D and 23F |
|  | X2 | Y2 | 23B, 23D, 23F and 23H |
|  | X2 | Y3 | 23D, 23F, 23G and 23I |
|  | X3 | Y1 | 23B, 23C, 23E and 23F |
|  | X3 | Y2 | 23B, 23C, 23H and 23I |
|  | X3 | Y3 | 23E, 23F, 23H and 23I |
| $z > \beta$ | X1 | Y1 | 23A, 23C, 23G and 23I |
|  | X1 | Y2 | 23A, 23C, 23G and 23I |
|  | X1 | Y3 | 23A, 23C, 23G and 23I |
|  | X2 | Y1 | 23A, 23C, 23G and 23I |
|  | X2 | Y2 | 23A, 23C, 23G and 23I |
|  | X2 | Y3 | 23A, 23C, 23G and 23I |
|  | X3 | Y1 | 23A, 23C, 23G and 23I |
|  | X3 | Y2 | 23A, 23C, 23G and 23I |
|  | X3 | Y3 | 23A, 23C, 23G and 23I |

Then, the signal control section 37 receives the magnetic field signals of the magnetic fields outputted from the sense coil groups in accordance with the control content on the signal detecting section 33 (in step S4 in FIG. 4) and outputs the received magnetic field signals to the signal recording section 34.

The signal recording section 34 temporarily records the magnetic field signals outputted from the signal control section 37. The source coil position analyzing section 35 estimates the three-dimensional position coordinates of each of the multiple source coils 21 based on the magnetic field signals recorded in the signal recording section 34 and outputs the result of the estimation to the inserted-shape image creating section 36 and signal control section 37 as the positional information signal. The inserted-shape image creating section 36 calculates the three-dimensional shape of the insertion section 11 based on the three-dimensional position coordinate information signals of the source coils 21 outputted from the source coil position analyzing section 35 and then creates the inserted-shape figure of the insertion section 11 from the calculated three-dimensional shape and outputs the figure as an inserted-shape figure signal. The monitor driving section 39 drives the monitor 9 based on the inserted-shape figure signal outputted from the inserted-shape image creating section 36 and renders the inserted-shape figure of the insertion section 11.

After that, in order to estimate the positions of the source coils 21 again, the source coil position analyzing section 35 estimates the three-dimensional position coordinates of each of the multiple source coils 21 based on the magnetic field signals recorded in the signal recording section 34, that is, the magnetic field signals of the magnetic fields outputted from the sense coil groups in accordance with the control content performed on the signal detecting section 33 by the signal control section 37 (in step S5 in FIG. 4) and outputs the result of the estimation to the signal control section 37 as positional information signals.

After that, for the source coils the approximate positions of which can be estimated at least of the multiple source coils 21 in the inserted-shape detecting probe 6, the sense coil groups are redefined by the signal control section 37 for receiving magnetic field signals of outputted magnetic fields based on the template as shown on TABLE 1 (in steps S2, S3, S4 and S5 in FIG. 4). For the source coils even the approximate positions of which cannot be estimated of the multiple source coils 21 in the inserted-shape detecting probe 6, the three-dimensional position coordinates of the source coils are estimated again by the source coil position analyzing section 35 based on the magnetic field signals of the twelve sense coils of the four sense coil groups 23A, 23C, 23G and 23I outputted from the sense coil groups (in steps S2, S6 and S1 in FIG. 4).

The signal control section 37 in the endoscope inserted-shape detecting apparatus 8 of the present embodiment controls the signal detecting section 33 based on the positional information signal outputted from the source coil position analyzing section 35 to select the layout of the sense coil groups 23A through 23I to be used for detecting the magnetic field generated by each of the multiple source coils 21 in the detecting probe 6. This operation allows the signal control section 37 to receive the magnetic field signals of the magnetic field outputted from the sense coil groups in positional relationships allowing estimating the position of each of the source coils 21 with high accuracy. Therefore, the endoscope inserted-shape detecting apparatus 8 of the present embodiment can render the inserted shape of the insertion section 11 more accurately than before, and a surgeon can perform the operation of inserting the endoscope 3 more smoothly as a result.

Second Embodiment

FIGS. 5 to 13 relate to a second embodiment of the present invention. The detail description of the parts having the same configuration as that of the first embodiment will be omitted herein. The same reference numerals are given to the same components as those of the first embodiment, the description of which will be omitted herein.

Figure 5:
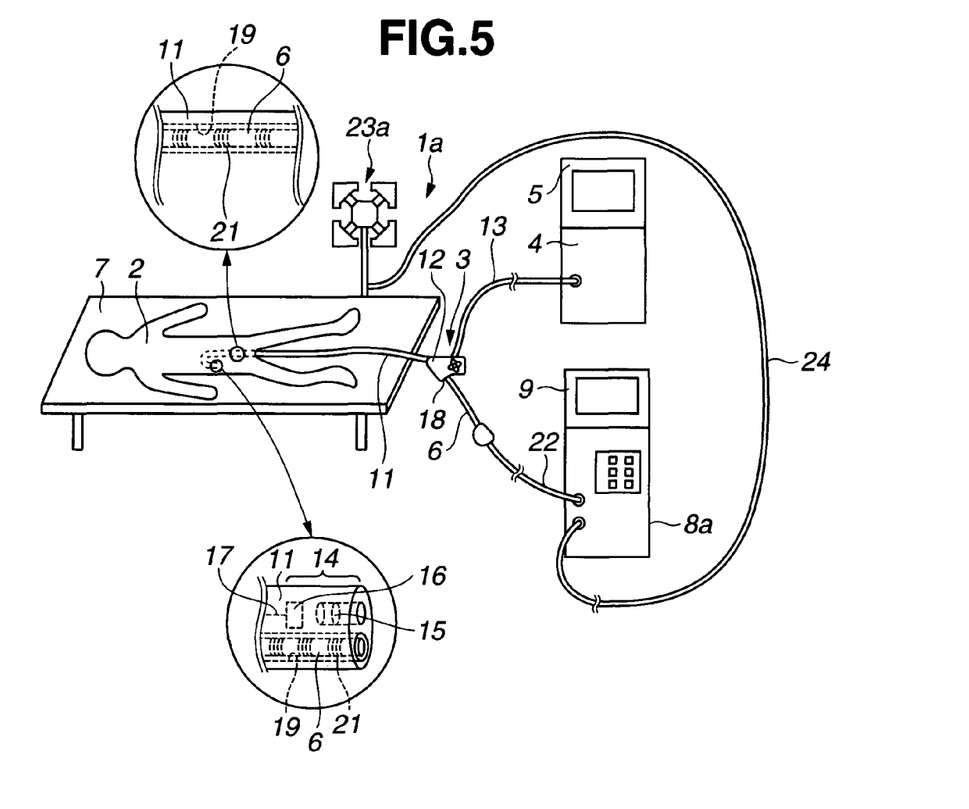
FIG. 5 is a diagram showing an entire configuration of an endoscopic system according to a second embodiment.
Figure 6:
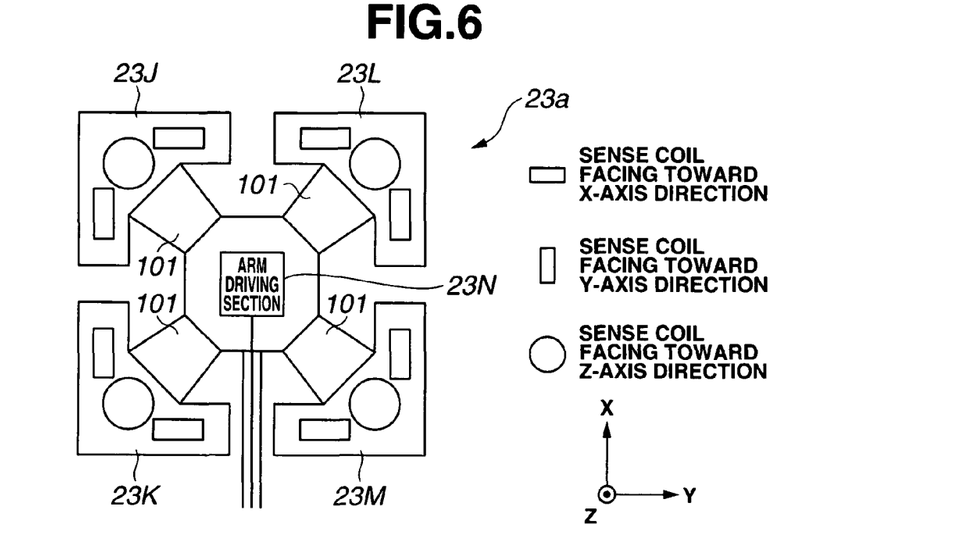
FIG. 6 is a diagram showing a configuration of a sense coil unit according to the second embodiment.
Figure 7:
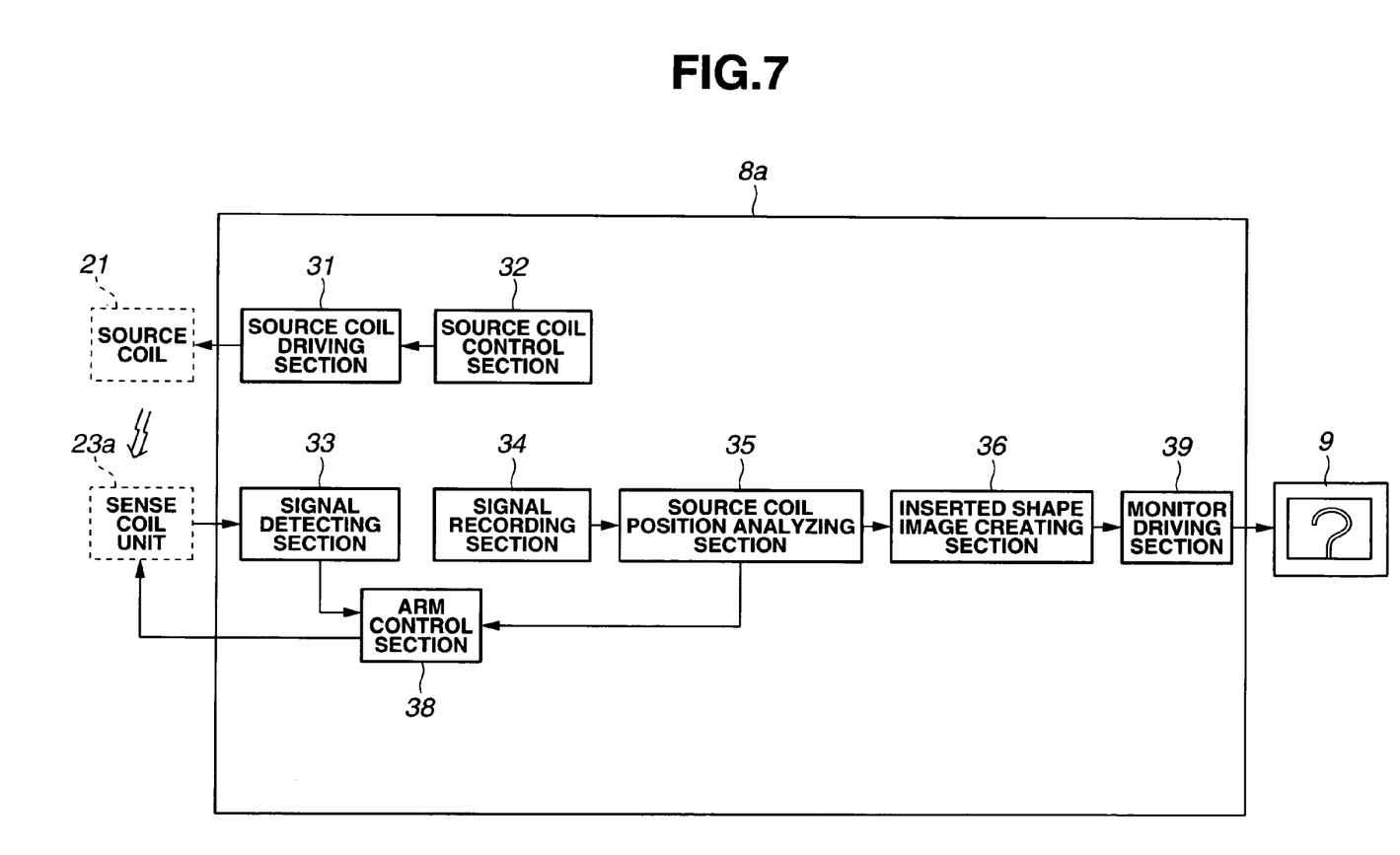
FIG. 7 is a block diagram showing an internal configuration of the endoscope inserted-shape detecting apparatus according to the second embodiment.
Figure 8:
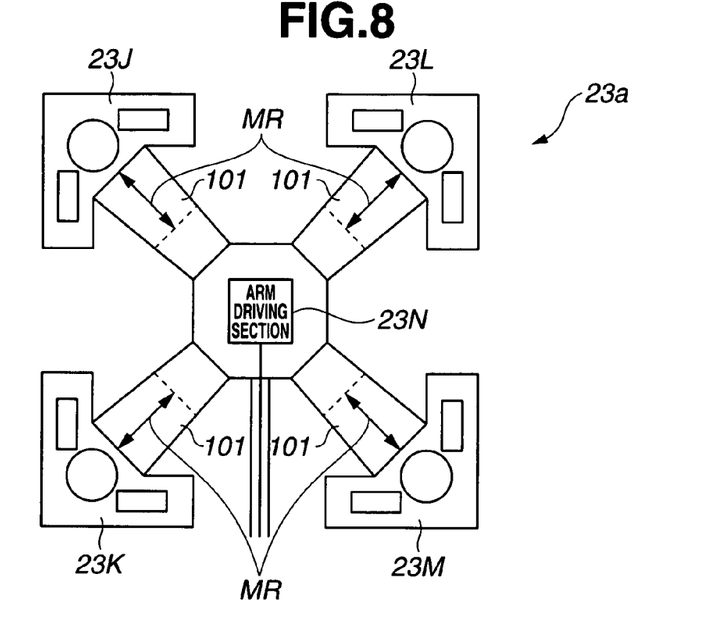
FIG. 8 is a diagram showing a case where the sense coil unit according to the second embodiment has a different state from that in FIG. 7.
Figure 9:
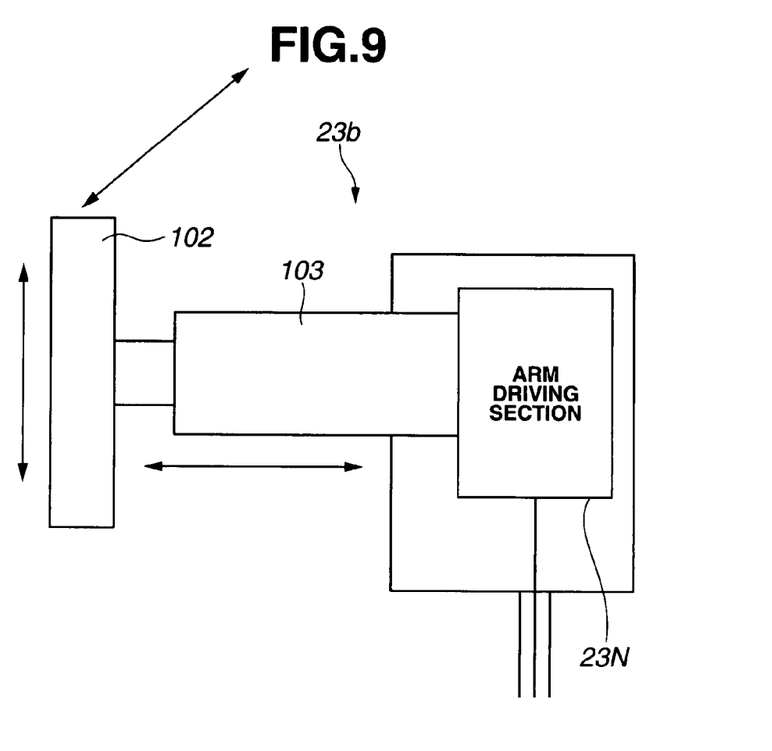
FIG. 9 is a diagram showing a configuration of a first variation example of the sense coil unit according to the second embodiment.
Figure 10:
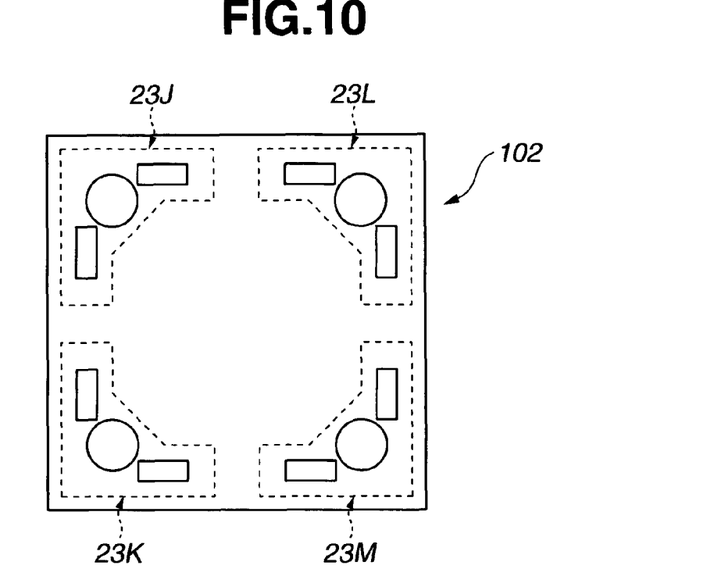
FIG. 10 is a diagram showing an example of the layout of sense coil groups in the sense coil unit in FIG. 9.
Figure 11:
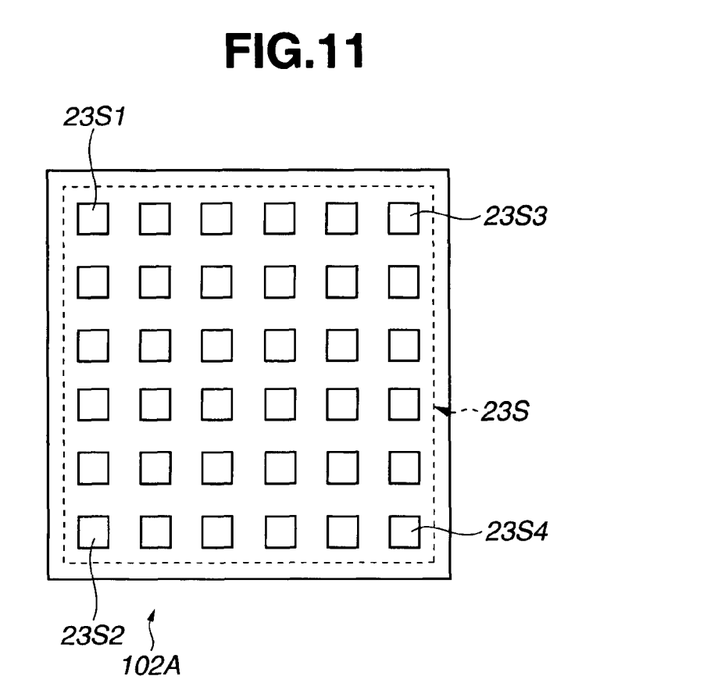
FIG. 11 is a diagram showing a configuration of a second variation example of the sense coil unit according to the second embodiment.
Figure 12:
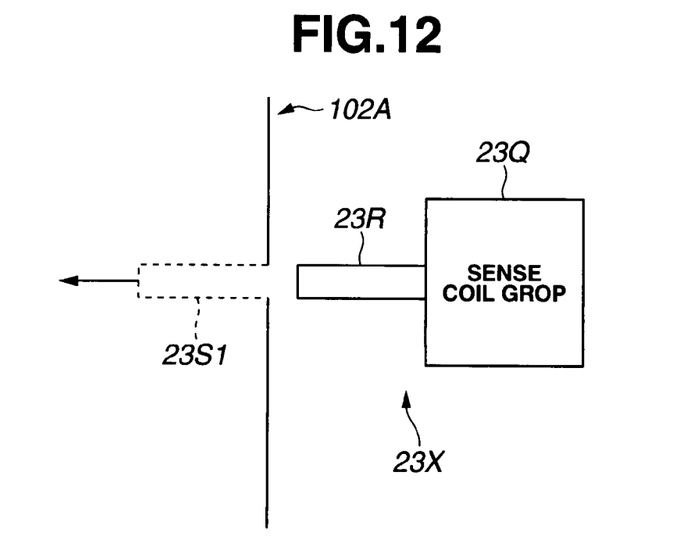
FIG. 12 is a diagram showing a configuration of a removable sense coil placed in the sense coil unit in FIG. 11.
Figure 13:
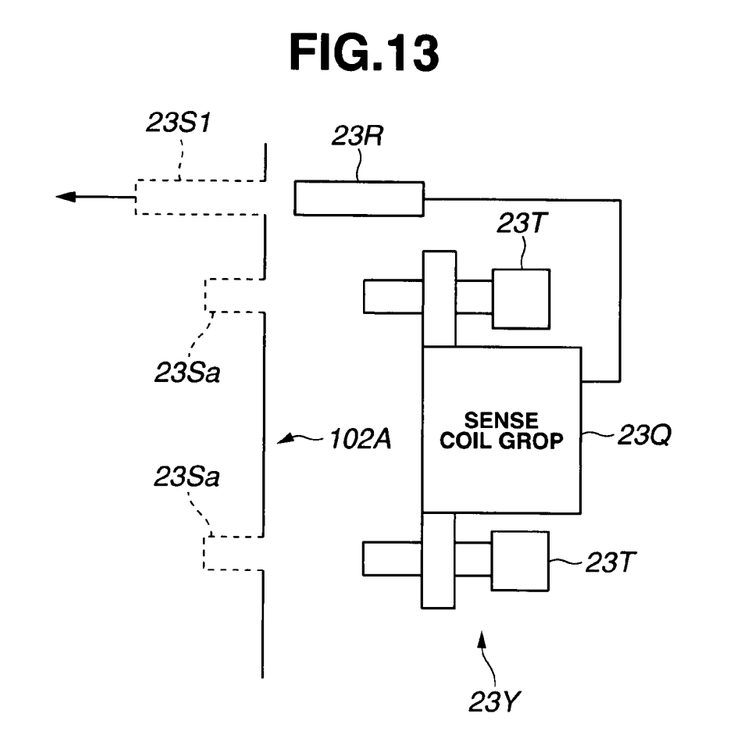
FIG. 13 is a diagram showing a configuration, which is different from the one in FIG. 12 in the removable sense coil placed in the sense coil unit in FIG. 11.

FIG. 5 is a diagram showing an entire configuration of an endoscopic system according to the second embodiment. FIG. 6 is a diagram showing a configuration of a sense coil unit according to the second embodiment. FIG. 7 is a block diagram showing an internal configuration of the endoscope inserted-shape detecting apparatus according to the second embodiment. FIG. 8 is a diagram showing a case where the sense coil unit according to the second embodiment has a different state from that in FIG. 7. FIG. 9 is a diagram showing a configuration of a first variation example of the sense coil unit according to the second embodiment. FIG. 10 is a diagram showing an example of the layout of sense coil groups in the sense coil unit in FIG. 9. FIG. 11 is a diagram showing a configuration of a second variation example of the sense coil unit according to the second embodiment. FIG. 12 is a diagram showing a configuration of a removable sense coil placed in the sense coil unit in FIG. 11. FIG. 13 is a diagram showing a configuration, which is different from the one in FIG. 12 in the removable sense coil placed in the sense coil unit in FIG. 11.

An endoscopic system 1a mainly includes, as shown in FIG. 5, an endoscope 3, a video processor 4, a monitor 5, an inserted-shape detecting probe 6, a bed 7, an endoscope inserted-shape detecting apparatus 8a, a monitor 9, and a sense coil unit 23a. The endoscope 3 picks up an image of the inside of a body cavity of a patient 2, which is a subject, within the body cavity and outputs the picked-up image of the inside of the body cavity as image pickup signals. The video processor 4 performs image processing on image pickup signals outputted from the endoscope 3 to output. The monitor 5 displays an image of a desired part picked up by the endoscope 3 based on image pickup signals outputted from the video processor 4. The patient 2 is laid down on the bed 7. In the inserted-shape detecting probe 6, multiple source coils 21, which are a part of the endoscope inserted-shape detecting apparatus 8a and are configured as multiple magnetic-field generating elements functioning as a magnetic-field generating section, are spaced apart at predetermined intervals.

The sense coil unit 23a, which is a magnetic-field detecting section provided outside of the endoscope inserted-shape detecting apparatus 8a as a part of the endoscope inserted-shape detecting apparatus 8a, is placed at a position as shown in FIG. 5 such that the magnetic field generated from each of the multiple source coils 21 provided in the inserted-shape detecting probe 6 to be inserted to a probe channel 19 of an insertion section 11 within a body cavity of the patient 2 laid on the bed 7 can be detected and is connected to the endoscope inserted-shape detecting apparatus 8a through a cable 24. The sense coil unit 23a includes four sense coil groups 23J, 23K, 23L and 23M as magnetic-field detecting elements, an arm driving section 23N and arms 101.

The sense coil group 23J includes, as shown in FIG. 6, three sense coils of a sense coil facing toward the X-axis direction, a sense coil facing toward the Y-axis direction and a sense coil facing toward the Z-axis direction. Other sense coil groups other than the sense coil group 23J also have the same configuration as that of the sense coil group 23J. The magnetic fields detected by the sense coil groups 23J to 23M are outputted to the endoscope inserted-shape detecting apparatus 8a as magnetic field signals. Each of the sense coil group 23J to 23M has, as shown in FIG. 6, a configuration in which the three sense coils are placed on a member in a substantial L-shape, and each of the members in the substantial L-shape is connected to the arm driving section 23N through the arms 101.

The arm driving section 23N is connected to the endoscope inserted-shape detecting apparatus 8a through the cable 24 by a signal line. The arm driving section 23N can drive the arms 101 based on the control content of the endoscope inserted-shape detecting apparatus 8a to change the positions of the sense coil groups 23J to 23M in a movable range MR of the arms 101.

As shown in FIG. 7, the endoscope inserted-shape detecting apparatus 8a internally includes a source coil driving section 31, a source coil control section 32, a signal detecting section 33, a signal recording section 34, a source coil position analyzing section 35, an inserted-shape image creating section 36, an arm control section 38 and a monitor driving section 39. The source coil driving section 31 drives each of the source coils 21. The source coil control section 32 controls the timing and frequencies for generating magnetic fields by the source coils 21 through the source coil driving section 31.

The arm control section 38, which is a control section, controls the arm driving section 23N to extend/contract the arms 101 based on magnetic field signals outputted from the signal detecting section 33 and positional information signals, which are signals outputted from the source coil position analyzing section 35 including the positional information of the source coils 21 and thus to change the positions of the sense coil groups 23J to 23M to have a predetermined positional relationship with the source coils 21. The control to be performed by the arm control section 38 is not limited to the control content described above but may be performed to receive, through the signal detecting section 33, magnetic field signals of the twelve sense coils of the four sense coil groups 23J to 23M based on the magnetic fields outputted by the sense coil groups and then control the arm driving section 23N based on the average value of the signal levels of the magnetic field signals of the twelve sense coils of the four sense coil groups to extend/contract the arms 101.

Next, with reference to FIGS. 5 to 8, an operation by using the endoscopic system 1a according to the present embodiment will be described.

First, a surgeon inserts the inserted-shape detecting probe 6 to the endoscope 3 from the probe insertion opening 18. After that, the surgeon connects the universal cord 13 of the endoscope 3 to the video processor 4 and connects the cable 22 of the inserted-shape detecting probe 6 and the cable 24 extending from the sense coil unit 23a to the endoscope inserted-shape detecting apparatus 8a and inserts the insertion section 11 of the endoscope 3 into a body cavity of the patient 2. Then, the CCD 16 picks up an image of the inside of the body cavity and outputs the picked up image of the inside of the body cavity as an image pickup signal. Then, the video processor 4 performs image processing thereon, for example, based on the image pickup signal outputted from the CCD 16 and outputs the image pickup signal after the image processing is performed, for example, to the monitor 5. The monitor 5 displays the image of the inside of the body cavity, which is picked up by the endoscope 3, based on the image pickup signal outputted from the video processor 4.

The source coil control section 32 of the endoscope inserted-shape detecting apparatus 8a controls the source coils 21 through the source coil driving section 31 such that the source coils 21 can generate magnetic fields at different times. The source coils 21 generate magnetic fields depending on the inserted shape of the insertion section 11 within the body cavity based on the control content of the source coil control section 32.

After each of the source coils 21 starts generating a magnetic field, the sense coil unit 23a first detects the magnetic field generated from each of the source coils 21 through the sense coil groups 23J to 23M at an initial state that the extension/contract state of the arms 101 is placed at the position shown in FIG. 6. The magnetic fields detected by the sense coil groups 23J to 23M are outputted to the endoscope inserted-shape detecting apparatus 8a through the cable 24.

The signal detecting section 33 converts the magnetic fields to magnetic field signals based on the magnetic fields outputted from the sense coil unit 23a and then amplifies to a signal-processable level and outputs the magnetic field signals. The signal recording section 34 temporarily records the magnetic field signals outputted from the signal detecting section 33. The source coil position analyzing section 35 estimates the three-dimensional position coordinates of each of the multiple source coils 21 based on the magnetic field signals recorded in the signal recording section 34 and outputs the result of the estimation to the arm control section 38 as positional information signals.

The source coil position analyzing section 35 further estimates the three-dimensional position coordinates of each of the multiple source coils 21 based on the magnetic field signals recorded in the signal recording section 34 and outputs the result of the estimation to the inserted-shape image creating section 36 as positional information signals. The inserted-shape image creating section 36 calculates the three-dimensional shape of the insertion section 11 based on the three-dimensional position coordinate information signals of the source coils 21 outputted from the source coil position analyzing section 35 and then creates the inserted-shape figure of the insertion section 11 from the calculated three-dimensional shape and outputs the figure as an inserted-shape figure signal. The monitor driving section 39 drives the monitor 9 based on the inserted-shape figure signal outputted from the inserted-shape image creating section 36 and renders the inserted-shape figure of the insertion section 11.

The arm control section 38 controls the arm driving section 23N to extend/contract the arms 101 based on the magnetic field signals outputted from the signal detecting section 33 and the positional information signals outputted from the source coil position analyzing section 35 such that the sense coil groups 23J to 23M can be placed at positions in predetermined positional relationships with predetermined source coils 21 and thus changes the positions of the sense coil groups 23J to 23M. The positions in predetermined positional relationships are positions where the magnetic field generated from a predetermined source coil 21, which generates a magnetic field at the strength of a substantially average value of all of the source coils, among the source coils 21 in the inserted-shape detecting probe 6 can be received by the sense coil groups 23J to 23M at a predetermined strength. The predetermined strength is a strength that does not reduce the accuracy for estimating the positions of the source coils 21 by the source coil position analyzing section 35, for example, the strength that does not cause magnetic saturation in any of the sense coil groups 23J to 23M and by which the magnetic field to be detected is not extremely weak.

When a predetermined source coil 21 generating a magnetic field at the strength of a substantially average value of those of all of the source coils is at a position extremely close to the sense coil unit 23a, the arm control section 38 controls the arm driving section 23N to extend the arm 101 such that the sense coil groups 23J to 23M can be positioned as shown in FIG. 8, for example, in order to prevent the reduction of the accuracy for estimating the position of the predetermined source coil 21 by the source coil position analyzing section 35 due to magnetic saturation.

When a predetermined source coil 21 generating a magnetic field at the strength of a substantially average value of those of all of the source coils is at a position far away from the sense coil unit 23a, the arm control section 38 controls the arm driving section 23N to extend the arm 101 such that the sense coil groups 23J to 23M can be positioned as shown in FIG. 8, for example, in order to prevent the reduction of the accuracy for estimating the position of the predetermined source coil 21 by the source coil position analyzing section 35 due to an extremely weak magnetic field detected.

When the distance from the position of a predetermined source coil 21 generating a magnetic field at the strength of a substantially average value of those of all of the source coils to the position of the sense coil unit 23a is a proper distance that allows detecting the magnetic field at the predetermined strength, the arm control section 38 controls the arm driving section 23N to contract the arm 101 such that the position of the sense coil groups 23J to 23M can be substantially the same as the initial state of the sense coil unit 23a as shown in FIG. 6, for example.

The control content to be performed by the arm control section 38 as described above is only required to perform for detecting the magnetic field generated from each of the source coils 21 in the inserted-shape detecting probe 6 at a strength that does not reduce the accuracy for estimating the positions of the source coils 21 by the source coil position analyzing section 35 and is not limited to the one to be performed on the sense coil groups 23J to 23M each including three sense coils. For example, the arm control section 38 may perform the control content as described above on the sense coil unit 23a having a structure in which each of the sense coils is connected to each of the arms 101.

The endoscopic system 1a of the present embodiment may be configured by using a sense coil unit 23b having a structure as shown in FIGS. 9 and 10 instead of the sense coil unit 23a.

The sense coil unit 23b, which is a magnetic-field detecting section, provided as a part of the endoscope inserted-shape detecting apparatus 8a and placed outside of the endoscope inserted-shape detecting apparatus 8a includes the arm driving section 23N, a sense coil section 102 and arms 103.

The sense coil section 102 has the sense coil groups 23J to 23M, each of which is placed at a position as shown in FIG. 10.

The arms 103 has a back-and-forth, horizontally and vertically movable configuration, and the position of the sense coil section 102 provided on the distal end side can be changed by controlling the arm driving section 23N provided on the proximal end side.

Because the sense coil unit 23b as a first variation example of the present embodiment has the structure as described above, the arm control section 38 controls the arm driving section 23N to extend/contract the arms 103 such that the sense coil groups 23J to 23M can be placed at positions in predetermined positional relationships where the magnetic field generated from a predetermined source coil 21, which generates a magnetic field at the strength of a substantially average value of all of the source coils, can be received by the sense coil groups 23J to 23M at a predetermined strength and thus changes the positions of the sense coil groups 23J to 23M. The predetermined strength is a strength that does not reduce the accuracy for estimating the positions of the source coils 21 by the source coil position analyzing section 35, for example, the strength that does not cause magnetic saturation in any of the sense coil groups 23J to 23M and by which the magnetic field to be detected is not extremely weak.

Alternatively, the sense coil section 102 of the sense coil unit 23b may have a structure as that of a sense coil section 102A shown in FIGS. 11 and 12 as a second variation example of the present embodiment.

The sense coil section 102A has a connector group 23S having multiple connectors like a connector 23 S1 shown in FIG. 11, for example. With the connector group 23S, the sense coil section 102A is removable from a removable sense coil 23X having a structure as shown in FIG. 12.

Each of the multiple connectors of the connector 23S1, for example, in the connector group 23S is connected to the endoscope inserted-shape detecting apparatus 8a through a signal line, not shown.

The removable sense coil 23X, which is a magnetic-field detecting element, includes a sense coil group 23Q having three sense coils of a sense coil facing toward the X-axis direction, a sense coil facing toward the Y-axis direction and a sense coil facing toward the Z-axis direction and a connector 23R removable from a connector such as the connector 23S1 in the connector group 23S.

The removable sense coil 23X is only required to be capable of receiving the magnetic fields generated from the source coils 21 and has a removable structure from a connector such as the connector 23S1 in the connector group 23S and is not limited to the one as shown in FIG. 12. The removable sense coil 23X may be configured as one like a sense coil 23Y shown in FIG. 13, for example. The removable sense coil 23Y includes a connecting section 23T around the sense coil group 23Q, and the connecting section 23T is removable from a connecting section 23Sa in the sense coil section 102A.

The sense coil group 23Q is not limited to the one having three sense coils as described above and may only include any one of the sense coils facing toward the X-axis direction, Y-axis direction and Z-axis direction.

Next, an operation in a case where the sense coil unit 23b has the sense coil section 102A will be described.

Before using the endoscope inserted-shape detecting apparatus 8a, a surgeon first connects the removable sense coil 23X to one of the connectors of the connector group 23S. Since the removable sense coil 23X can be connected to multiple connectors in the connector group 23S at the same time, the following description assumes that one removable sense coil 23X is connected to connectors 23S1, 23S2, 23S3 and 23S4 at four corners of the connector groups 23S as shown in FIG. 11.

After that, when the surgeon starts the components of the endoscopic system 1a, each of the source coils 21 generates a magnetic field depending on the inserted shape of the insertion section 11 in a body cavity based on the control content by the source coil control section 32.

After each of the source coils 21 starts generating a magnetic field, the sense coil unit 23b detects the magnetic field generated by each of the source coils 21 through the removable sense coils 23X provided at the four corners of the connector group 23S first. The magnetic fields detected by the four removable sense coils 23X mounted at the four corners of the connector group 23S are outputted to the endoscope inserted-shape detecting apparatus 8a through the cable 24.

The signal detecting section 33 converts the magnetic fields to magnetic field signals based on the magnetic fields outputted from the sense coil unit 23b and then amplifies to a signal-processable level and outputs the magnetic field signals. The signal recording section 34 temporarily records the magnetic field signals outputted from the signal detecting section 33. The source coil position analyzing section 35 estimates the positions and number of the connected removable sense coils 23X in the connector group 23S and the three-dimensional position coordinates of each of the multiple source coils 21 based on the magnetic field signals recorded in the signal recording section 34 and outputs the result of the estimation to the arm control section 38 as positional information signals.

The arm control section 38 controls the arm driving section 23N to extend/contract the arms 103 based on the magnetic field signals outputted from the signal detecting section 33 and the positional information signals outputted from the source coil position analyzing section 35 such that the four removable sense coils 23X mounted at the four corners of the connector group 23S can be placed at positions in predetermined positional relationships with predetermined source coils 21 and thus changes the position of the sense coil unit 23b. The positions in predetermined positional relationships are positions where the magnetic field generated from a predetermined source coil 21, which generates a magnetic field at the strength of a substantially average value of all of the source coils, among the source coils 21 in the inserted-shape detecting probe 6 can be received by the four removable sense coils 23X at a predetermined strength. The predetermined strength is a strength that does not reduce the accuracy for estimating the positions of the source coils 21 by the source coil position analyzing section 35, for example, the strength that does not cause magnetic saturation in any of the four removable sense coils 23X and by which the magnetic field to be detected is not extremely weak.

Notably, even after the position of the sense coil unit 23b is changed under the control of the arm control section 38, the accuracy for estimating the positions of the source coils 21 by the source coil position analyzing section 35 may be reduced by the generation of magnetic saturation caused by the magnetic field generated by a predetermined source coil 21, which generates a magnetic field at a strength of a substantially average value of those of all of the source coils, in one of the removable sense coils 23X at the four corners of the connector group 23S, for example. In this case, the inserted-shape image creating section 36 outputs an inserted-shape figure signal to the monitor driving section 39 such that a string having a description prompting to change the connected positions or reduce the number of the connected removable sense coils 23X, for example, can be displayed over the inserted-shape figure of the insertion section 11 of the endoscope 3 based on the positional information signal outputted from the source coil position analyzing section 35.

The monitor driving section 39 drives the monitor 9 based on the inserted-from figure signal outputted from the inserted-shape image creating section 36 and renders the string having the description prompting a surgeon to change the connected position or reduce the number of the connected removable sense coils 23X, for example, over the inserted-shape figure of the insertion section 11.

When a state that no magnetic saturation occurs in any of the removable sense coils 23X is obtained after that by the change of the connected position or reduction of the number of the connected removable sense coils 23X by the surgeon with reference to the string, the inserted-shape image creating section 36 stops the display of the string based on the positional information signal outputted from the source coil position analyzing section 35 and outputs the inserted-shape figure of the insertion section 11 after the change of the connected position or reduction of the number of the connected removable sense coils 23X is performed to the monitor driving section 39 as an inserted-shape figure signal.

Furthermore, even after the position of the sense coil unit 23b is changed under the control of the arm control section 38, the accuracy for estimating the positions of the source coils 21 by the source coil position analyzing section 35 may be reduced by an extremely weak magnetic field generated by a predetermined source coil 21, which generates a magnetic field at a strength of a substantially average value of those of all of the source coils, to be detected by the removable sense coils 23X at the four corners of the connector group 23S, for example. In this case, the inserted-shape image creating section 36 outputs an inserted-shape figure signal to the monitor driving section 39 such that a string having a description prompting to change the connected positions or increase the number of the connected removable sense coils 23X, for example, can be displayed over the inserted-shape figure of the insertion section 11 of the endoscope 3 based on the positional information signal outputted from the source coil position analyzing section 35.

The monitor driving section 39 drives the monitor 9 based on the inserted-from figure signal outputted from the inserted-shape image creating section 36 and renders the string having the description prompting a surgeon to change the connected position or increase the number of the connected removable sense coils 23X, for example, over the inserted-shape figure of the insertion section 11.

A state that the detected magnetic fields are not extremely weak in any of the removable sense coils 23X is obtained after that by the change of the connected position or increase of the number of the connected removable sense coils 23X by a surgeon with reference to the string. Under the state, the inserted-shape image creating section 36 stops the display of the string based on the positional information signal outputted from the source coil position analyzing section 35 and outputs the inserted-shape figure of the insertion section 11 after the change of the connected position or increase of the number of the connected removable sense coils 23X is performed to the monitor driving section 39 as an inserted-shape figure signal.

The endoscope inserted-shape detecting apparatus 8a of the present embodiment has the configuration in which the arm control section 38 controls the sense coil unit 23a or sense coil unit 23b such that the sense coil groups 23J to 23M or removable sense coils 23X can receive the magnetic field generated by a predetermined source coil 21, which generates a magnetic field at the strength of a substantially average value of all of the source coils, at a predetermined strength that does not cause magnetic saturation and is a strength by which the magnetic field to be detected is not extremely weak. In other words, the arm control section 38 selects the layout of the sense coil groups 23J to 23M or removable sense coils 23X to be used for detecting the magnetic field generated by a predetermined source coil 21, which generates a magnetic field at the strength of a substantially average value of all of the source coils, by controlling the sense coil unit 23a or sense coil unit 23b based on the positional information signal outputted from the source coil position analyzing section 35. Therefore, the endoscope inserted-shape detecting apparatus 8a of the present embodiment can estimate the position of each of the source coils 21 with high accuracy, and the inserted shape of the insertion section 11 can be rendered more accurately than before. As a result, a surgeon can perform the inserting operation of the endoscope 3 more smoothly.

What is claimed is:

1. An endoscope inserted-shape detecting apparatus, comprising:

a magnetic-field detecting section including multiple magnetic-field detecting elements for detecting magnetic fields generated by multiple magnetic-field generating elements provided in an insertion section of an endoscope, the multiple magnetic-field detecting elements being placed at predetermined positions;

a signal detecting section creating magnetic field signals in accordance with strength of the magnetic fields detected by the magnetic-field detecting elements and outputting the created magnetic field signals;

a magnetic-field generated position estimating section estimating the positions of the magnetic field generating elements based on the magnetic field signals; and a control section for determining whether the strength of the magnetic field signal associated with a predetermined magnetic field generating element is within a predetermined range, setting a first subset of magnetic-field detecting elements if the strength is within the predetermined range, or setting a second subset of the magnetic-field detecting elements if the strength of the magnetic field signal is not within the predetermined range, as a group to be used for detecting magnetic field signals.

2. The endoscope inserted-shape detecting apparatus according to claim 1, wherein the control section further controls the signal detecting section so as to output only the magnetic field signal from the group of magnetic-field detecting elements.

3. The endoscope inserted-shape detecting apparatus according to claim 2, wherein the multiple magnetic-field detecting elements are placed in a matrix form in the magnetic-field detecting section.

4. The endoscope inserted-shape detecting apparatus according to claim 3, wherein the multiple magnetic-field detecting elements are placed in the magnetic-field detecting section in a state that the magnetic-field generated position estimating section can estimate the three-dimensional position coordinates of each of the multiple magnetic field generating elements.

5. The endoscope inserted-shape detecting apparatus according to claim 2, wherein the multiple magnetic-field detecting elements are placed in the magnetic-field detecting section in a state that the magnetic-field generated position estimating section can estimate the three-dimensional position coordinates of each of the multiple magnetic field generating elements.

6. The endoscope inserted-shape detecting apparatus according to claim 1, wherein the control section further controls to change the positions where the magnetic-field detecting elements are placed based on the magnetic field signals.

7. The endoscope inserted-shape detecting apparatus according to claim 6, wherein the multiple magnetic-field detecting elements are placed in a matrix form in the magnetic-field detecting section.

8. The endoscope inserted-shape detecting apparatus according to claim 7, wherein the multiple magnetic-field detecting elements are placed in the magnetic-field detecting section in a state that the magnetic-field generated position estimating section can estimate the three-dimensional position coordinates of each of the multiple magnetic field generating elements.

9. The endoscope inserted-shape detecting apparatus according to claim 6, wherein the multiple magnetic-field detecting elements are placed in the magnetic-field detecting section in a state that the magnetic-field generated position estimating section can estimate the three-dimensional position coordinates of each of the multiple magnetic field generating elements.

10. The endoscope inserted-shape detecting apparatus according to claim 1, wherein, if the magnetic-field generated position estimating section cannot estimate the positions of the magnetic field generating elements, the control section further sets each magnetic-field detecting element placed at a corner of the magnetic-field detecting section as the group of the magnetic-field detecting elements.

11. The endoscope inserted-shape detecting apparatus according to claim 10, wherein the multiple magnetic-field detecting elements are placed in a matrix form in the magnetic-field detecting section.

12. The endoscope inserted-shape detecting apparatus according to claim 11, wherein the multiple magnetic-field detecting elements are placed in the magnetic-field detecting section in a state that the magnetic-field generated position estimating section can estimate the three-dimensional position coordinates of each of the multiple magnetic field generating elements.

13. The endoscope inserted-shape detecting apparatus according to claim 10, wherein the multiple magnetic-field detecting elements are placed in the magnetic-field detecting section in a state that the magnetic-field generated position estimating section can estimate the three-dimensional position coordinates of each of the multiple magnetic field generating elements.

14. The endoscope inserted-shape detecting apparatus according to claim 1, wherein the multiple magnetic-field detecting elements are placed in a matrix form in the magnetic-field detecting section.

15. The endoscope inserted-shape detecting apparatus according to claim 14, wherein the multiple magnetic-field detecting elements are placed in the magnetic-field detecting section in a state that the magnetic-field generated position estimating section can estimate the three-dimensional position coordinates of each of the multiple magnetic field generating elements.

16. The endoscope inserted-shape detecting apparatus according to claim 1, wherein the multiple magnetic-field detecting elements are placed in the magnetic-field detecting section in a state that the magnetic-field generated position estimating section can estimate the three-dimensional position coordinates of each of the multiple magnetic field generating elements.

17. The endoscope inserted-shape detecting apparatus according to claim 1, wherein the strength within the predetermined range is a strength within a range in which magnetic saturation does not occur at each magnetic-field detecting element belonging to the group of magnetic-field detecting elements, and in which a magnetic field detected at each magnetic-field detecting element belonging to the group of magnetic-field detecting elements does not become extremely weak.

18. The endoscope inserted-shape detecting apparatus according to claim 1, wherein the control section selects the combination of the magnetic-field detecting elements to be set as the group of the magnetic-field detecting elements by referring to a template in which an estimation result of the magnetic-field generated position estimating section and a state of placement of the magnetic-field detecting element suited for detecting the magnetic-field signal are associated to each other in advance.

* * * * *